United States Patent [19]

Hodgen

[11] Patent Number: 4,740,364

[45] Date of Patent: Apr. 26, 1988

[54] PREDICTING PREDISPOSITION TO OSTEOPOROSIS

[75] Inventor: Gary D. Hodgen, Norfolk, Va.

[73] Assignee: Eastern Virginia Medical Authority, Norfolk, Va.

[21] Appl. No.: 780,739

[22] Filed: Sep. 27, 1985

[51] Int. Cl.$^4$ ............................................. G01N 33/48
[52] U.S. Cl. ......................................................... 424/9
[58] Field of Search ....................................... 424/9, 11

[56] References Cited

PUBLICATIONS

Abbasi et al., JAMA, vol. 255, No. 12, pp. 1600–1604, Predicting the Piedisposition to Osteoporosis (1986).
Hodgen et al I, Amer. J. N. Obsterics & Gynecology, vol. 127, No. 6, pp. 581–584 (1977).
Erb et al, J. Animal Science, vol. 30, No. 1 (1970).
Urago; Acta Pat. Hol. Jpn, vol. 32, No. 5, pp. 759–770 (1982).
Hodgen et al II, J. Animal Science, vol. 26, No. 3 (1967).
Miller et al, Calcif. Tissue Int. (38) pp. 62–65 (1986).

Primary Examiner—Glennon H. Hollrah
Assistant Examiner—D. L. Dinner
Attorney, Agent, or Firm—Millen & White

[57] ABSTRACT

A method of providing a diagnostic indicia which is predictive of the risk of a non-osteoporotic human being contracting osteoporosis as a consequence of being in a long-term hormonally agonadal state, which comprises the steps of determining the average ratio of calcium to creatinine in the urine or in the blood of that person, during a period when the person is ingesting only foodstuff sources of calcium and vitamin D, while in a hormonally gonadal state, and also while in a hormonally agonadal state; determining the magnitude of the difference in the ratio obtained in the latter state compared to the former state, a large difference being predictive of a high risk of that person contracting osteoporosis.

21 Claims, No Drawings

PREDICTING PREDISPOSITION TO OSTEOPOROSIS

BACKGROUND OF THE INVENTION

This invention relates to a method of predicting the risk of a non-osteoporotic human being contracting osteoporosis as a consequence of being in a long-term hormonally agonadal state and to a test kit for practicing this method.

Osteoporosis is a predictable sequalae in primates and other mammals to a long-term hormonally agonadal condition. Although it most frequently manifests itself in post-menopausal women in association with their longevity beyond the years of gonadal activity, it can occur in castrated males and females and in pre-menopausal women on long-term GnRH agonist or antagonist therapy, e.g., for the treatment of endometriosis or precocious puberty, or in instances of protracted amenorrhea due to extremes of exercise, anorexia or irradiation with or without chemotherapy affecting ovarian or testicular functions.

Few naturally occurring diseases adversely affect the quality and longevity of so many human lives as the sequelae to severe estrogen deficiency in the post-menopausal years. The prevalence of the disease is evident from the fact that about one woman in four will experience at least one bone fracture attributable to calcium depletion of the bone by the time she reaches the age of 60 years.

The benefits of estrogen replacement therapy (ERT) for conservation of bone calcium, prevention of hot flashes and amelioration of urogenital tissue atrophy in most postmenopausal and ovariectomized women are well known. Although most postmenopausal women gain obvious benefits from ERT, particularly when a family history, skeletal type, habits and genetic predisposition suggest that the individual is at significant risk, there are several reasons why mass ERT for all post-menopausal women is not medically acceptable to most practitioners. First, and perhaps most important, even though progestins are often overlapped sequentially with the estrogen in ERT, in order to shed proliferative endometrium and thereby reduce the risk of endometrial carcinoma, ERT regimens remain controversial with regard to incidences of endometrial carcinoma and cardiovascular complications. Second, women usually prefer to avoid menstruation beyond the natural menopause. However, some uterine bleeding is manifested by most of the women on current ERT/progestin regimens. Finally, a smaller but significant number of women do not require ERT in the postmenopausal years or can gain considerable symptomatic relief from progestins alone. Therefore, some diagnostic evaluation is employed by most physicians before instituting ERT; albeit highly subjective at this time.

Evaluations by bone densitometry for discrimination of those women most needing estrogens prophylactically can come too late to avert progressive osteoporosis, because such assessments are retrospective and the bone loss irreversible. Accordingly, a reliable predictive test to identify perimenopausal women who are highly vulnerable to the negative sequelae of severe estrogen deficiency would be useful to practitioners in deciding for whom, when and how to implement ERT, progestin treatment or a combination regimen.

Accordingly, it is an object of this invention to provide a method of obtaining from a non-osteoporotic human being an indicia which is reliably predictive of the magnitude of the risk of that patient ultimately contacting osteoporosis as a consequence of being in a long-term hormonally agonadal state.

Another object is to provide materials and specific reagents for kits for obtaining the aforesaid indicia.

Upon further study of the specification and appended claims, further objects and advantages of this invention will become apparent to those skilled in the art.

SUMMARY OF THE INVENTION

In a method aspect, this invention relates to a method of determining an index which is predictive of the predisposition of a non-osteoporotic human being contracting osteoporosis, which comprises the steps of:

(a) determining the average ratio of calcium to creatinine in the urine or in the blood of that person while in a hormonally gonadal state, during a period when that person is not ingesting calcium supplements or vitamin D;

(b) determining the average ratio of calcium to creatinine in the urine of that person, when that ratio was determined in that person's urine in step (a) or in the blood of that person when that ratio was determined in that person's blood in step (a), while that person is in the hormonally agonadal state and during a period when that person is not ingesting calcium supplements and vitamin D; and (c) determining the magnitude of the difference in the ratio obtained in step (b) compared to step (a), a small difference being predictive of a low risk and a large difference being predictive of a high risk of that person contracting osteoporosis.

In preferred aspects, the human being is a peri- or post-menopausal female in a hormonally agonadal state and the hormonally gonadal state in step (a) is induced prior to step (a) by estrogen replacement therapy; or the human being is a pre-menopausal female and the agonadal state is temporarily induced by administering an amount of either a GnRH antagonist or agonist to the female effective to create the acute (reversible) hypoestrogenic (agonadal) state; or the human being is an endometriotic pre-menopausal female scheduled for long-term treatment of that condition with a GnRH antagonist or agonist; or the human being is a female and the agonadal state of step (b) is created by surgically removing the female's ovaries and step (b) is conducted at least several days after the surgery, when the patient has reached an acute hypoestrogenic state; or the human being is a precocious puberic child scheduled for treatment of that condition with a GnRH agonist or antagonist; or the human being is a male scheduled for GnRH agonist or antagonist treatment or surgical orchidectomy and step (a) is conducted prior to surgery and step (b) is conducted at least several days after surgery; or the human being is a post-pubertal fertile female scheduled to be transformed into a long-term infertile state by the administration thereto of a contraceptive amount of GnRH agonist or antagonist.

In an article of manufacture aspect, this invention relates to materials and reagents for a kit adapted for obtaining urine samples from a human being while in a hormonally gonadal state and in a hormonally agonadal state comprising:

(a) a plurality of containers adapted for storing sequentially therein a plurality of urine samples;

(b) means comprising at least one container containing an amount of a GnRH agonist or antagonist, in a pharmaceutically effective carrier, effective when administered intranasally to a hormonally gonadal human being to render that person temporarily and reversibly hormonally agonadal.

In preferred aspects, the materials and reagents for kit comprises at least 6 containers for urine samples; the containers for the GnRH agonist or antagonist can be adapted to self-administer the contents thereof in a unit dosage amount, e.g., by injection or intranasally as a mist or aerosol, and more preferably, the GnRH antagonist or agonist is contained in a single container, which preferably is a plastic nasal mist squeeze bottle and the pharmaceutical carrier is a liquid. In general, a preferred exception to self-administration is the injectable unit dosage form.

DETAILED DISCUSSION

Although a variety of conditions and diseases can induce osteoporosis, presently the vast majority of such cases are initiated by the natural menopause in women or by gonadectomy in women and men. Therefore, in preferred aspects, this method is directed to peri-menopausal females, pre-menopausal females scheduled for surgical removal of her ovaries and post-menopausal females who have not yet manifested overt symptoms of osteoporosis.

Another class of females for whom the method of this invention is a useful tool is pre-menopausal females scheduled for long-term treatment with a GnRH antagonist or agonist, either for the treatment of endometriosis, for contraception, or other medical conditions preferring reversible supression of gonadal steroidogensis.

Other classes of females for which the method of this invention can be used to acknowledge are hyperactive teenage athletes whose puberty has been delayed by their athletic activity and females who have undergone chemotherapy or radiation therapy which has destroyed some or all of the ovarian follicles.

Other classes of human beings for which the method of this invention is useful are males scheduled for medical or surgical orchidectomies and precocious puberic children, both male and female, scheduled for treatment of that condition with a GnRH agonist or antagonist.

Although this invention is directed to human beings, it will be apparent to those skilled in the art that it will similarly be useful in predicting the onset of osteoporosis in other animals, e.g., non-human primates, dogs, horses and cats.

In one step of the method of this invention, the steady-state creatinine and calcium levels in the selected body fluid of a human being, i.e., blood or urine, are determined while that person is in a hormonally gonadal state. There are well-known conventional methods for doing so. See, e.g., Hodgen, G. D. et al., J. Anim. Sci., 1967 26:586; Erb, R. E. et al., ibid, 1970 30:79; Nordin, B. C. C., *Clin. Endocrinol.* 8:55, 1978.

Because calcium blood and urine levels in human beings can be significantly influenced by the amounts thereof which are ingested by the individual, the person being tested should not vary his eating habits during the test period and should not ingest dietary supplement sources of calcium or vitamin D, which also affects the results obtained. To ensure against the introduction of this variable into the method of this invention, the patient should be warned not to alter or otherwise prevented, e.g., by hospitalization, from altering his normal eating habits during the test period, to avoid dietary supplements containing calcium or vitamin D, and to not change exercise habits radically.

Also, because calcium and creatinine levels vary significantly from day to day, more so in the blood and less so in the urine, it is also important that the calcium and creatinine levels be determined on successive days and under the same conditions. Therefore, these levels should be determined on at least two, preferably 3 and most preferably for from 3 to 5 successive days, and preferably also at the same time of the day, e.g., the first urine void each morning.

Obviously, because the calcium and creatinine levels of the various body fluids vary tremendously, the same body fluid should be employed in the testing of those levels while the human being is in the gonadal state and while in the agonadal state.

If the human being to be tested is initially in an active gonadal (steroidogenic) state, nothing need be done in preparation for conducting the method of this invention besides determining the calcium and creatinine levels in the selected body fluid on the selected days. However, if the person is temporarily in an agonadal state, e.g., an oligomenorrheic female who has missed one or more menstrual periods, or is permanently in an agonadal state, e.g., a post-menopausal female who is not yet osteoporotic, that person must be in or brought into an active-like gonadal state (steroidogenically) when practicing the method of this invention. In the case of a oligomenorrheic female, her gonadal status can be determined by blood assay for circulating estradiol and/or by sonographic measurement of uterine endometrium thickness and ovarium follicular size. If the female is agonadal, e.g., post-menopausal or is oligomenorrheic in a temporarily agonadal state, she can be brought to a gonadally active-like ERT state, until the aforesaid test or tests establish the patient is at least temporarily in a gonadal-like (steroidogenically) state. The base-line calcium and creatinine levels of the person in the gonadal-like restored state can then be determined according to the method of this invention.

In another step in the method of this invention, the base-line ratio of calcium to creatinine concentrations in the selected body fluid of the human being in the gonadal state is determined. The magnitude of the rise in this numerical value while the patient is in an agonadal state, is diagnostically indicative of the propensity of that person to ultimately become osteoporotic as a results of being in a long-term hormonally agonadal state.

If the human being becomes agonadal surgically, this determination can be made within a few days, e.g., 3 and preferably 4 or more days, after the surgical castration. Similarly, if the patient is a post-menopausal female who was temporarily transformed into a gonadal state by ERT, the cessation of that therapy will rapidly (unless the therapy is accomplished surgically with a long-acting implant) revert the patient to an agonadal state, e.g., within about 3 or more days. Any doubt can be resolved sonically by measurement of uterine endometrium thickness, ovarian follicular size and/or circulating estrogen levels. Typically, a gonadal state in a female requires at least 40 and ordinarily about 80–120 pg/ml of blood plasma or serum estradiol or biologically equivalent amounts of other estrogens. Conversely, circulating estradiol (or comparable exogenous female hormone levels of a patient on ERT) levels of at least 40 pg/ml is required to ensure a gonadal state adequate to prevent significant bone calcium loss (leading to osteoporosis).

If the human being is not spontaneously, i.e., either surgically or through cessation of ERT, transformed into an agonadal state, that patient must next be temporarily transformed into that state, e.g., by the administration thereto of sufficient GnRH antagonist or agonist to substantially completely suppress gonadol steroid production, i.e., so that blood serum estradiol level drops to below 40 pg/ml and preferably to an even lower level, e.g., 10 pg/ml or less.

An example of GnRH agonists is $(imB_{21})$-$DHis^6Pro^9$-NET]-GnRH. Others are known in the prior art.

Other agonists include:

[(ImB21(-D-His$^6$, Pro$^9$-NEt]LHRH

[D-Trp$^6$, N$\delta$MeLeu$^7$, Pro$^9$-NEt]LHRH

[D-Ser(TBU)$^{6,}$ Pro$^9$-NEt]LHRH

[D-Nal$_{(2)}$$^6$, Pro$^9$-NEt]LHRH

[D-Ser(Bu$^6$)AzGly$^{10}$]LHRH

An example of GnRH antagonists is (Ac-p-Cl-Ph$^1$-p-Cl-Phe$^2$, D-(Trp$^3$), D-Arg$^6$, D-Ala$^{10}$)NET-GnRH. Others are known in the prior art.

Other antagonists include:

| | | | | | | | | | | |
|---|---|---|---|---|---|---|---|---|---|---|
| D2Nal Ac | DPhe 4Cl | D3Pal | Ser | Arg | D2Nal | Leu | Arg | Pro | DAla | NH$_2$ |
| D2Nal Ac | DPhe 4Cl | D3Pal | Ser | Arg | DGlu A.A. | Leu | Arg | Pro | DAla | NH$_2$ |
| DNal$_2$ Ac | Phe 4FD | DTr | Ser | Tyr | DArg | Leu | Arg | Pro | Gly | NH$_2$ |

[N—Ac—d-Na(2)$^1$, d-pCl—Phe$^2$, d-Trp$^3$, d-hArg(Et$_2$)$^6$, d-Ala$^{10}$]LHRH

Ac[D-B—Nal$^1$, D-p-Cl—Phe$^2$, D-Trp$^3$, D-Arg$^6$, D-Ala$^{10}$]LHRH

| | | | | | | | | | | |
|---|---|---|---|---|---|---|---|---|---|---|
| Ac—D-Nal | D-a Me—4-Cl—Phe | D-Pal | Ser | Tyr | D-Arg | Leu | N$^a$—Ipr—Lys | Pro | D-Ala | NH$_2$ |

When a GnRH antagonist is employed, an agonadal state can usually be achieved within about 3 days if initiating medication. When a GnRH agonist is employed, usually a longer medication period is required before the agonadal state is achieved, e.g., often 10 days or sometimes longer. In either case, confirmation that this state has been reached, e.g., by measurement of blood estradiol levels and/or sonogram measurement of uterine endometrium thickness or ovarian follicular diameter, is recommended.

Any compound(s) which induces hypoestrogenic conditions consistent with increased excretion of calcium may be used in this diagnostic test.

Once the human being is in an agonadal state, the calcium and creatinine levels are determined in the same body fluid thereon in which these levels were determined while the person was in a gonadally active-like state, i.e., in the same manner employed in the first step of the method of this invention. Here also, steady-state or average levels must be determined by conducting such measurements with the same body fluid collected on a plurality, e.g., at least 3 and preferably 3-5 days, which preferably are successive, under constant conditions of calcium, vitamin D foodstuff-only ingestion and exercise. No other medications can be superimposed.

Having determined the steady-state, base-line ratio of calcium to creatinine levels in the selected body fluid of the human being while in a gonadally active-like state and while in an agonadal state, the increase in the latter ratio over the former ratio is next determined. The magnitude of that increase is diagnostically indicative of the magnitude of the risk of that human being becoming osteoporotic as a result of being in a long-term agonadal-like state. Although no precise value can be assigned to that level of risk, an increase of 40% or more in that ratio is indicative of a significant risk of that person contracting osteoporosis while in a long-term agonadal state.

More specifically, if the increase in calcium secretion rate numerically ($\Delta$) is high, a 0–25% increase in the aforesaid ratio is indicative of a sufficiently low risk that ERT probably is not necessary to prevent rapid onset of osteoporosis; a 25% to 60% increase in that ratio is indicative of a moderate risk, and either ERT should be initiated or the person carefully monitored for the appearance of overt symptoms of early stages of osteoporosis; and a greater than 60% increase is indicative of a high risk, so that ERT therapy should be initiated immediately, if that person already is in a permanent agonadal state or as soon as that person reaches that state.

Conversely, if the numerical increase ($\Delta$) in calcium excretion rate which occurs when that person is transformed from a gonadal state to an agonadal state is relatively low, a 0–15% increase in the calcium-creatinine ratio is diagnostically indicative of a low risk; a 15–40% increase is indicative of a moderate risk and a greater than 40% increase in that ratio is indicative of a high risk of that person becoming osteoporotic while in a long-term agonadal state.

In its article of manufacture embodiment, this invention relates to materials, reagents and kits for practicing the method of this invention.

Necessarily, if the body fluid selected for measuring calcium and creatinine levels is blood, the collection of the blood in order to practice the method of this invention must be conducted under medical supervision. Therefore, if the patient must be temporarily be transformed from an agonadal state to a gonadal state with ERT or from a gonadal state to an agonadal state with a GnRH antagonist or agonist, this can also be done conveniently under medical supervision prior to taking the appropriate blood samples. In such a case, materials and reagents for practicing this aspect of the method of this invention would be of relatively little advantage. On the other hand, if urine is the selected body fluid, it can be collected by the patient, who can also self-administer the medication required to achieve or gonadal or an agonadal state. In such a situation, provision of materials, reagents and kits is definitely advantageous in practicing the method of this invention, both from the standpoint of patient convenience and from the point of view of ensuring that the patient is provided appropriate instruction and treatment or self-administers the medication properly and that the urine samples are correctly identified.

An example of such materials, reagents and kits is one comprising a plurality of numerically numbered, resealable collectors for urine, e.g., flexible polyethylene bottles or bags which are freezable, each having up to 1000 cc capacity, and/or which contain a conventional preservative for urine which inhibits microbial growth while the sample is in the patient's custody, e.g., 0.2% thimerosal. If the urine samples are taken only after the patient has been diagnosed as being in a gonadal or in a agonadal state, as few as three such containers would be required. However, if the urine samples are to be used to monitor daily the transition of the patient from one state to the other, as many as 10-21 or more such containers would be provided.

If the patient is to self-medicate him or herself, the reagent(s) will also, optionally, comprise the requisite medication required to practice the method of this invention on the particular class of patient involved, e.g., 5 tablets or capsules of 100 mcg. estradiol for daily ingestion and/or a nasal spray squeeze bottle containing a GnRH antagonist or agonist in an inert fluid carrier at a concentration effective to deliver into a nostril, with one and preferably 2 or 3 squeezes of the bottle, either once a day or twice a day, an amount of the GnRH agonist or antagonist effective to render the human being agonadal within the anticipated number of days.

In alternative embodiments, the test kit will contain medication incorporated in another delivery system, e.g., the appropriate plurality of adhesive skin patches containing the medication in an intradermal and delivery system for application to the skin on successive days, daily or twice daily; an appropriate plurality of suppositories for administration of the medication rectally or vaginally on successive days daily or twice daily; or an inhaler for delivery of the medication as an aerosol, once or twice daily on successive days. Primarily, it is contemplated that the medication may be injected intramuscularly or subcutaneously, using, e.g., time release capsules in an injectable form, e.g., in an ampoule.

The materials, reagents and kits optionally and preferably also contains instructions for collecting and storing the urine samples and, when the materials and kits comprise medication, instructions for self-administration thereof.

An example of materials, reagents and kits of this invention intended for use by a gonadal female who is to be converted temporarily into an agonadal state with a GnRH antagonist or agonist is a box with lid containing ten sequentially numbered 50 cc wide-mouthed polyethylene bottles as urine collectors, with removable snap on lids, each containing 1.0 mg. of thimerosal as preservative. Preferably, the box contains dividers adapted to maintain the bottles in an upright position in the box when filled. Also contained in the box is a nasal mist squeeze bottle containing an amount of a GnRH antagonist or agonist, at a concentration in an inert, physiologically acceptable carrier effective to deliver, when the bottle is squeezed twice while the open top thereof is inserted into the nostril, an amount of the GnRH antagonist or agonist effective to render the female agonadal within 5 days. The parenteral method of administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1

In a study, to experimentally evaluate the method of this invention, primate models were employed to determine whether acute GnRH antagonist treatment allowed prospective identification of those individuals most acutely vulnerable to a negative calcium balance during overt estrogen deficiency. The study also was used to determine whether daily treatment with high-dose clomiphene citrate would be sufficiently estrogenic to abate urinary calcium loss and to sustain vaginal and perineal tissues after ovariectomy and provide these beneficial effects without inducing endometrial proliferation and menstruation after progestin withdrawal. A comparison was made against the effects of conjugated equine estrogens.

Materials and Methods

Adult female rhesus monkeys (4.2 to 8.6 kg) were housed and maintained in environmentally controlled laboratory conditions as described previously. See Hodgen, G. D. et al., *Endocrinology* 90:896–900, 1972; Goodman, A. L. et al., ibid, 100:155, 1977. Urine collections were made between 0600 h and 0900 h, after overnight fasting and provision of distilled drinking water. As necessary, urine was taken from the bladder by suprapubic aspiration. Similarly methods have proven reliable in both human and animal metabolic studies of calcium and creatinine excretion in urine. See Nordin, B. E. C., *Clin. Endocrinol* 8:55, 1978; Nordin, B. E. C., et al., *Brit. Med. J.* 280:5212, 1980; Horsman, A., et al., *Calcified Tissue Research* 22(supp):217, 1977; Hodgen, G. D., et al. *J. Anim. Sci.* 26:586, 1967; and Erb, R. E., et al., *J. Anim. Sci.*, 30:79, 1970. Here, the ratio of calcium to creatinine was calculated on the final 3 days of a 10 day control versus treatment regimen.

In Phase I of the protocol, the objective was to achieve acute suppression of estrogens in circulation by GnRH antagonist treatment (N=19) and to compare the urinary calcium:creatinine ratio to pretreatment controls. A 2 mg/kg/day, I. M. dose of GnRH antagonist [(Ac-pClPhe$^1$, pClPhe$^2$, DTrp$^3$, DArg$^6$, DAla$^{10}$)-GnRH]was employed. This dose was sufficient to suppress serum gonadotropins below measureable limits in long-term castrate monkeys within 48 to 72 hours. Even 1 mg/kg/day I.M. greatly depleted circulating estradiol levels in intact females. See Kenigsberg et al, 1984. GnRH antagonist treatments were initiated at any point on days 1 to 5 of the monkeys' menstrual cycles. Phase II was a nontreatment rest interval of 90 days, permitting resumption of the ovarian/menstrual cycle. Lastly, Phase III achieved hypoestrogenic status by bilateral surgical ovariectomy during the early follicular phase. Among these acute castrates, the post-castration urinary calcium:creatinine ratio was compared to that observed under acute GnRH antagonist therapy in Phase I, as well as to that of intact controls. Concurrently, 3.5 ml of femoral blood was taken on the final day of each control or treatment regimen for measurement of estradiol levels.

Urinary calcium:creatinine ratios were re-assessed at 88 to 90 days and 178 to 180 days after ovariectomy. Thereafter, ERT was given to monkeys assigned randomly. The treatment interval was 30 days and in either of two forms: 1) conjugated equine estrogens (CEE, Premarin, Ayerst Laboratories, New York, N.Y., N=8, 0.15 mg/day, po) and 2) clomiphene citrate (CC, Serophene, Serono Laboratories, Randolph, MA, N=7, 48 mg/day, po).

On days 21 to 30 of the ERT, a silastic implant (sc) providing progesterone at midluteal phase levels (5 ng/ml of serum) was administrated. After 8 to 10 days of progesterone treatment, urinary calcium excretion was measured; then, progesterone treatment was discontinued to test for withdrawal bleeding.

In order to assess the peripheral estrogenicity of these ERT regimens, weekly vaginal epithelial smears were evaluated histologically; concurrently, coloration (red- = estrogenization) of the perineum was recorded photographically.

The dose of CEE was chosen to approximate the high dose range for women receiving ERT. For convenience, human CEE pills of 0.3 mg were cut-in-half, providing a monkey dose of 0.15 mg. On a body weight basis, this corresponds to a human dose of about 1.5 mg of CEE daily. For CC, the 48 mg dose was selected on the basis of a previous study (below) in long-term castrate monkeys. These ovariectomized monkeys (n=20) were divided into 4 groups of 5 each and given CC tablets for one month as follows: (1) 12 mg/day; (2) 24 mg/day; (3) 48 mg/day; or (4) daily placebo controls. Daily blood samples were assayed for gonadotropins, estradiol and prolactin by established methods. Laparotomy and hysterotomy were performed to assess endometrial proliferation on days 15 and 30. Monkeys were checked daily for menstrual flow, vaginal cornification and redness of the perineal skin Significant differences in numerical responses were detected by use of the F statistic for groups of equal or unequal size Tests were analyzed at $p<0.05$ and $p<0.01$ levels. Linear regression analysis allowed comparison of the degree of negative calcium balance during GnRH antagonist treatment versus after ovariectomy.

Results

The severe acute depletion of ovarian estrogen secretion in these primates, whether by GnRH antagonist treatment or ovariectomy, led to increased ($p<0.05$) calcium excretion. At the end of Phase I, after 10 days of GnRH antagonist treatment, serum estradiol had declined to 24+7 pg/ml, compared to 97+36 pg/ml among intact controls ($p<0.01$). The calcium:creatinine ratio in urine rose from 0.11+0.03 (controls) to 0.18+0.05 ($p<0.05$) after 8 to 10 days of GnRH antagonist administration, an increase of 63.6%. Following resumption of ovulation in 18 of 19 females during the recovery interval of Phase II, ovariectomy (Phase III) caused an even greater ($p<0.05$) negative calcium balance than the GnRH antagonist, i.e., a rise in calcium:-creatinine ratio from 0.10+0.02 to 0.21+0.04 among intact controls and castrates, respectively, an increase of 110%. Concurrently, serum estradiol levels declined from 86+28 pg/ml (controls) to 13+14 pg/ml at 10 days after ovariectomy ($p<0.01$).

An ongoing negative calcium balance occurred after ovariectomy, although a significant decline ($p<0.05$) in the urinary calcium:creatinine ratio was observed during the initial 6 months after ovariectomy, i.e., from about 0.21 to about 0.16. Administration of either CEE or CC reversed ($p<0.01$ and $p<0.05$, respectively) this status by reducing calcium loss in urine. CEE therapy was more effective ($p<0.05$) than CC at the doses employed (0.15 vs 48 mg/day). In fact, CEE treatments were associated with a trend ($p<0.05$) toward a positive shift in the urinary calcium:creatinine ratio relative to intact controls. None of the treatments had a significant effect on creatinine excretion in urine ($p<0.05$).

After making the above observations, it was of interest to determine whether individual monkeys who manifested the highest calcium:creatinine ratios during acute suppression by the GnRH antagonist were among those expressing the greatest negative calcium balance soon after ovariectomy. 3 groups of animals were separated according to the degree of elevation of the calcium: creatinine ratio during Phase I (acute GnRH antagonist treatment). There was a strong correlation ($r=+0.87$, $p<0.01$) between monkeys having high urinary calcium:creatinine ratios during GnRH antagonist suppression of ovarian estrogen secretion and after ovariectomy, less so in the mid ($r=+0.42$, $p<0.05$) and low ($r=+0.14$, $p>0.05$) ratio groups. Indeed, among the latter group, 5 of 7 individuals showed no effect of either the GnRH antagonist or ovariectomy on calcium excretion.

Both CEE and CC had profound estrogenic effects on peripheral estrogen-dependent tissues. Both ERT regimens induced cornified epithelial cells in the vagina and enhanced redness of the previously blanched perineum of long-term castrate monkeys. One month of CEE administration proliferated endometrial tissues, as evidenced by withdrawal bleeding after progesterone treatment. In contrast, CC did not cause endometrial proliferation and, moreover, there was no menstrual flow following equivalent progesterone treatment.

Negative feedback suppression of FSH and LH secretion occurred in long-term ovariectomized monkey receiving 48 mg of CC daily. This response manifested broad individual variation with lower doses of CC inhibiting blood levels of FSH and LH less markedly. Serum estradiol remained 12 pg/ml; prolactin levels were not affected by CC treatments.

Discussion

The results of this model study extends our earlier opinion that menopausal primate models may be useful paradigms for estrogen-calcium metabolism in women. See, Hodgen, G. D., et al., *Am. J. Obstet. Gynecol.*, 127:581, 1977. In particular, it is of some considerable significance that acute (reversible) pituitary-ovarian suppression by the GnRH antagonist, with its attendant increases in calcium excretion, allowed identification of those individual monkeys most likely to have high urinary calcium:creatinine ratios after ovariectomy.

As demonstrated here, this discrimination was made after a seven day regimen of the GnRH antagonist which achieves a "medical hypophysectomy" status within 48 to 72 hours.

Example 2

A peri-menopausal woman, e.g., age 43, having regular menstrual cycles all her life until the last 12 months during which she has had only 6 irregular menstrual cycles, is determined to have circulating estrogens of less than 40 pg/ml blood plasma and has a uterus which by sonogram exhibits an atrophic endometrium and upon examination is found to have minimal thick cervical mucus and a vaginal epithelium which is not cornified.

The patient is prescribed to receive 100 μg. ethinylestradiol per os daily for 30 days and is given 5 polyethylene bottles as described hereinabove containing urine preservative and instructed to collect about 25 cc sample of the first void of urine on the 25th day (day 1) following the first day of ethinylestradiol ingestion, collecting the urine in the correspondingly numbered urine collection bottle. The patient is further instructed to store the urine samples in a refrigerator or freezer until her next appointment, at which time she is to return the five specimens for analysis. Calcium and creatinine levels of samples 3–5 are determined and the ratio of the former to the latter calculated. Upon her return with the five urine specimens, there 2 mg/kg/day of the GnRH antagonist of Example 1 is administered to the patient for 6 successive days. On the first such day, the patient is given 6 additional polyurethane urine collection bottles, numbered 6–12, with the same instructions for urine collection on the next succeeding 6 days and for storage of the collected samples. When the latter urine samples are returned by the patient, the calcium and creatinine levels of samples 10–12 are determined according to the procedure described by Nordin, B. E. C., *Clin. Endrocrinol.* 8:55, 1978, and their ratio to each other calculated.

If the calcium:creatinine ratio increases from the patient's estrogenized status to her hypoestrogenic status induced by the GnRH antagonist by at least 60%, the patient is diagnosed at high risk for early onset of osteoporotic disease and deserves counseling on immediate estrogen replacement therapy as may be medically indicated.

If the aforesaid ratio increases by about 25–60%, the patient is advised to return for re-evaluation within 12 to 24 months or, because the patient is at moderate risk for osteoporosis, she is counseled to consider ERT later on, either for prophylaxis against osteoporosis or for other manifestations of hypoestrogenic state, e.g., hot flashes or other physiological or psychological manifestations, if these symptoms appear subsequently. Moreover, although there may not yet be a need for ERT to prevent calcium loss from the bones of such patients, there is no urgency in instituting the therapy so that delaying doing so for 2–5 years after onset of menopause may be adequate with periodic bone densitometry.

If the aforesaid ratio increases by no more than 25%, the patient is diagnosed at minimum risk of contracting osteoporotic disease due to hypoestrogenic status. Therefore, ERT therapy is not immediately required and the patient is counseled accordingly as to the likelihood of the patient thereafter acquiring osteoporosis.

Whatever the diagnosis, bone densiometry is also indicated as a means of monitoring the bone calcium status of the patient.

Example 3

The same patient as in Example 2 is examined immediately after the last day of her most recent menstruation. The pelvic examination reveals abundant and thin cervical mucus and a vaginal epithelium containing cornified cells. The same procedure is employed as in Example 2, except that the transient estrogen therapy is omitted. The same diagnostic procedure is followed with the urine samples collected by the patient.

Example 4

A post-menopausal female, e.g., age 48, who has not menstruated for one year and who exhibits overt symptoms of a hypoestrogenic state upon pelvic examination but bone densitometry reveals no evidence of osteoporosis and who exhibits no other overt symptoms thereof, is given 5 consecutively numbered polyethylene bottles and instructed on the collection of urinary samples in the same manner as Examples 2 and 3. When the patient returns with the samples, estradiol ERT (100 mcg/day/per os) is initiated for 30 days. The patient is then given 5 additional urine collection bottles, numbered 6–10, and instructed to collect urine in the same manner on the last 5 days of the ERT. When the patient returns with the urine samples then those previously collected are analyzed for their calcium and creatinine levels and the ratio of the former to the latter is determined and the percentage increase in the ratio of those levels in samples 1–5 compared to the ratio of those levels in samples 6–10 is determined. In the case of an already post-menopausal female, a shift of 40% of more in the ratio is indicative of a high risk of the patient ultimately contracting osteoporosis; a shift of 25–40% is indicative of a moderate risk; and a shift of less than 25% is indicative of a low risk.

Example 5

With the same class of patient as in Example 3, follow the same procedure except administer intranasally as a mist (1–5 mg/kg/day) the GnRH antagonist [DHis$^6$-(imB$_{21}$), Pro$^9$-NET]-GnRH for 21 days and instruct the patient to collect the urine samples on days 16–21. The same dosages can be used in a similar manner parenterally.

Example 6

Follow the procedure of Example 3 with a 2 year old female precocious puberic child manifesting cyclic menstrual flow, enlarged breasts (e.g., Tanner III), pubic hair and a bone age of 8 or 9 years beyond her chronological age, scheduled for pituitary ovarium suppression with a GnRH agonist or antagonist until about the age 11. The increase in calcium:creatinine ratio will be predictive of how rapidly her bone calcium may be lost as a result of the therapy.

Example 7

Follow the procedure of Example 2 with a female gymnast, age 18, manifesting exercise-induced amenorrhea Tanner II or III breasts and only one or two menses since the age 13, with blood diagnosis indicating abnormal status. The increase in urinary calcium:creatinine ratio will be indicative of the extent of damage to her skeletal system as a result of a continuation of her amenorrhetic state.

Example 8

Following the collection procedures described in the preceding examples, collect the urine before the surgery of a pre-menopausal female scheduled to have her ovaries removed surgically, and after surgery, for a 5 day period not less than 5 days and desirably not more than 6 months after surgery. The increase in the calcium:creatinine ratio therein will be predictive of the likelihood of the patient incurring rapid onset of osteoporosis as a result of the surgery.

Example 9

Follow the procedure of Example 8 with a male in his early 60's, with prostatic carcinoma and scheduled for long-term treatment with a GnRH agonist or antagonist to suppress pituitary function. Collect the urine samples of the patient before therapy and 30 days after therapy has begun. The percentage increase in calcium:creatinine ratio will be indicative of the likelihood of the patient becoming osteoporotic as a result of the therapy. The effects of surgical orchiectomy are similarly diagnosed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of determining the predisposition of a non-osteoporotic human being toward contracting osteoporosis, which comprises the steps of:
    (a) measuring the average ratio of calcium to creatinine in the urine or blood of that person while in a hormonally gonadal state, during a period when that person is not ingesting supplemental calcium or vitamin D;
    (b) measuring the average ratio of calcium to creatinine in the urine or blood of that person, when that ratio was measured in the urine of that person in step (a) or in the blood of that person when the ratio was measured in the blood of that person in step (a), while that person is in a hormonally agonadal state, during a period when that person is not ingesting supplemental calcium or vigamin D; and
    (c) determining the magnitude of the difference in those ratios, and correlating this difference with the level of risk of that person contracting osteoporosis.

2. A method according to claim 1, wherein the human being is a pre-menopausal female in a hormonally agonadal state.

3. A method according to claim 1, wherein in steps (a) and (b) it is the urine of the female in which the average ratio of calcium to creatinine is measured.

4. A method according to claim 2, wherein the agonadal state is temporarily and reversibly induced by administering an amount of GnRH agonist or antagonist to the female effective to achieve an acute hypoestrogenic state in the female.

5. A method according to claim 4, wherein the GnRH agonist is [DHis$^6$(inB$_{21}$), Por$^9$-NET]-GnRH.

6. A method according to claim 2, wherein the agonadal state is temporarily and reversibly induced by administering an amount of GnRH antagonist to the female effective to achieve an acute hypoestrogenic state in the female.

7. A method according to claim 6, wherein the antagonist is (Ac-p-ClPhe$^1$, p-ClDPhe$^2$, D-Trp$^3$, D-Arg$^6$, D-Ala$^{10}$)NETGnRH.

8. A method according to claim 7, wherein in steps (a) and (b) it is the urine of the female in which the average ratio of calcium to creatinine is measured.

9. A method according to claim 2, wherein the female is an endometriotic pre-menopausal female scheduled for long-term treatment of that condition with a GnRH agonist or antagonist.

10. A method according to claim 9, wherein in steps (a) and (b) it is the urine of the female in which the average ratio of calcium to creatinine is measured.

11. A method according to claim 2, wherein the agonadal state of step (b) is created surgically by removing the female's ovaries and step (b) is conducted at least several days after the surgery, when the patient has reached a hypoestrogenic state.

12. A method according to claim 11, wherein in steps (a) and (b) it is the urine of the female in which the average ratio of calcium to creatinine is measured.

13. A method according to claim 2, wherein the female is peri- or post-menopausal and in a hormonally agonadal state and the hormonally gonadal state of step (a) is achieved in the female prior to step (a) by estrogen replacement therapy.

14. A method according to claim 13, wherein in steps (a) and (b) it is the urine of the female in which the average ratio of calcium to creatinine is measured.

15. A method according to claim 1, wherein the human being is a precociously puberic child scheduled for treatment of that condition with a GnRH agonist or antagonist.

16. A method according to claim 1, wherein the human being is a male scheduled for medical or surgical orchidectomy, wherein step (a) is conducted prior to treatment or surgery and step (b) is conducted at least several days after treatment or surgery.

17. A method according to claim 2, wherein the female is a fertile adult scheduled for treatment by the administration thereto of a contraceptive amount of GnRH agonist or antagonist to achieve a long-term infertile state in the female.

18. A method according to claim 17, wherein in steps (a) and (b) it is the urine of the female in which the average ratio of calcium to creatinine is measured.

19. A method according to claim 3, wherein steps (a) and (b) are conducted with first void urine collected on at least three successive days.

20. A method according to claim 1, wherein the human being is a pre-menopausal or peri-menopausal female in a hormonally agonadal state and the gonadal state is temporarily and reversibly induced by administering an amount of GnRH agonist or antagonist to the female effective to achieve an acute hypoestrogenic state in the female.

21. A method of determining the predisposition of a nonosteoporotic female human being toward contracting osteoporosis, which comprises the steps of:
    (a) measuring the average ratio of calcium to creatinine in the urine or blood of that person while in a hormonally gonadal state, during a period when that person is not ingesting supplemental calcium or vitamin D;

(b) measuring the average ratio of calcium to creatinine in the urine or blood of that person, when that ratio was measured in the urine of that person in step (a) or in the blood of that person when the ratio was measured in the blood of that person in step (a), while that person is in a hormonally agonadal state, during a period when that person is not ingesting supplemental calcium or vitamin D; and (c) determining the magnitude of the difference in those ratios, and correlating this difference with the level of risk of that person contracting osteoporosis.

* * * * *